US00PP15379P3

(12) United States Plant Patent
Utecht

(10) Patent No.: US PP15,379 P3
(45) Date of Patent: Nov. 30, 2004

(54) ***GERANIUM* PLANT NAMED 'FIP 469'**

(50) Latin Name: *Pelargonium zonale*
Varietal Denomination: Fip 469

(75) Inventor: Angelika Utecht, Montabaur (DE)

(73) Assignee: Florfis AG (CH)

( * ) Notice: Subject to any disclaimer, the term of this patent is extended or adjusted under 35 U.S.C. 154(b) by 0 days.

(21) Appl. No.: 10/715,431

(22) Filed: Nov. 19, 2003

(65) Prior Publication Data

US 2004/0123361 P1 Jun. 24, 2004

(30) Foreign Application Priority Data

Dec. 19, 2002 (CA) ..... PBR 02-3405

(51) Int. Cl.[7] ..... A01H 5/00
(52) U.S. Cl. ..... Plt./329
(58) Field of Search ..... Plt./329, 328

(56) References Cited

PUBLICATIONS

GTITM UPOV ROM Citation for 'Fip 469', as per DE PBR PEL 01650, Oct. 15, 2001.*
Canadian Plant Breeder's Rights Application No. 02–3405 filled Dec. 23, 2002.
German Plant Breeder's Rights application No. PEL 1650 filed Jun. 26, 2000.
Published denomination of German Plant Breeder's Rights Application No. PEL 1650, Oct. 15, 2001.
Published grant of German Plant Breeder's Rights Application No. PEL 1650, Jan. 17, 2002.

* cited by examiner

*Primary Examiner*—Kent Bell

(57) ABSTRACT

A new and distinct cultivar of *geranium* plant named 'Fip 469', particularly characterized by the combined features of bluish-pink, semi-double flowers with small white eyes, medium green foliage with weak zonation, vigorous growth, tall plant habit, and medium to late spring flowering response.

1 Drawing Sheet

Genus and species of the plant claimed: Hybrid *Pelargonium zonale* L'Héritier
Variety denomination: 'Fip 469'

BACKGROUND OF THE INVENTION

The present invention comprises a new and distinct cultivar of *geranium*, botanically known as *Pelargonium zonale*, and hereinafter referred to by the cultivar name 'Fip 469'.

'Fip 469' is a product of a planned breeding program which had the objective of creating new zonal *geranium* cultivars with pink flower color, medium green foliage, vigorous growth habit, and good outdoor performance.

'Fip 469' originated from a hybridization made by the inventor, Angelika Utecht, in a controlled breeding program in Hillscheid, Germany, in 1997. The female parent was the commercial variety 'Highfield's Festival' (unpatented), having pink semi-double flowers, foliage with slight zonation, and vigorous growth. The male parent of 'Fip 469' was an unpatented hybrid seedling no. K96-1059-1, characterized by pink single-type flowers with eyes on petals, uniform, dark-green foliage, and about medium sized plant habit.

'Fip 469' was selected as one flowering plant within the progeny of the stated cross by Angelika Utecht in 1998 in a controlled environment in Moncarapacho, Portugal. The first act of asexual reproduction of 'Fip 469' was accomplished when vegetative cuttings were taken from the initial selection in the fall of 1998 in a controlled environment in Moncarapacho, Portugal, by, or under the supervision of, Angelika Utecht.

Horticultural examination of plants grown from cuttings of the plant initiated in May, 1999, in Hillscheid, Federal Republic of Germany, and continuing thereafter, has demonstrated that the combination of characteristics as herein disclosed for 'Fip 469' are firmly fixed and are retained through successive generations of asexual reproduction.

'Fip 469' has not been observed under all possible environmental conditions. The phenotype may vary significantly with variations in environment such as temperature, light intensity and day length.

BRIEF SUMMARY OF THE INVENTION

The following observations, measurements, and comparisons describe plants grown in Hillscheid, Germany, under greenhouse conditions which approximate those generally used in commercial practice.

The following traits have been repeatedly observed and are determined to be basic characteristics of 'Fip 469' in combination distinguish this *geranium* as a new and distinct cultivar:

1. Bluish-pink semi-double flowers with white eyes;
2. Medium sized inflorescences with long, thick, reddish peduncles;
3. Medium-green foliage with weak to medium zonation;
4. Vigorous growth, tall, moderately tight, and
5. Medium to late spring flowering response.

Of the many commercial cultivars known to the present inventor, the most similar ones in comparison to 'Fip 469' is the variety 'Fip 749' (U.S. Plant Pat. No. 14,084), the variety 'Fislypso' (U.S. Plant Pat. No. 11,162), the variety 'Fisfany' (U.S. Plant Pat. No. 10,876), and the variety 'Fisrobrav' (U.S. Plant Pat. No. 13,249).

In comparison to 'Fip 749', 'Fip 469' has a similar or slightly deeper main flower color, more distinct reddish veins at the bases of upper petals, but only weakly reddish colored peduncles, medium-green, instead of dark-green, foliage, taller plant habit, and later beginning of flowering.

In comparison to 'Fislypso', 'Fip 469' has a slightly more pink, less bluish hue of flower color, somewhat more distinct zonation on leaves, and much taller plant habit.

In comparison to 'Fisfany', 'Fip 469' lacks the red eyes on petals, and grows distinctly taller.

In comparison to 'Fisrobrav', 'Fip 469' has a similar main flower color, but no red-purple eyes on petals. Furthermore, 'Fip 469' grows more vigorously, and develops really tall plants.

BRIEF DESCRIPTION OF THE DRAWING

The accompanying photographic drawing shows typical flower and foliage characteristics of 'Fip 469' with colors being as true as possible with an illustration of this type.

The photographic drawing shows the top part of a flowering potted plant of 'Fip 469'.

DETAILED BOTANICAL DESCRIPTION

The measurements were taken in Hillscheid, Germany, in mid May, 11 weeks after planting of rooted cuttings. The plants were growing in 14 cm pots, they had not been pinched.

In the following description color references are made to The Royal Horticultural Society Colour Chart. The color values were determined indoors from plants growing in a green-house in May 2003 in Hillscheid, Germany.

INFLORESCENCE

Umbel:

*Shape.*—Semi-spherical.
*Average diameter.*—115 mm.
*Average depth.*—55–60 mm.
*Peduncle length.*—278 mm.
*Peduncle color.*—Light green, RHS 143 B, outdoors a slight tinge of brown may occur, RHS 179 B.
*Pedicel.*—35 mm in length.
*Pedicel color.*—Green, RHS 143 B, at the lower end, upper part brownish, RHS 181 A.
*Number of flowers per umbel.*—About 40–60.

Corolla:

*Average diameter.*—51 mm.
*Average depth.*—8 mm.
*Form.*—Semi-double type.
*Shape.*—Round outline, with the upper petals about the same size as the lower petals.
*Number of petals.*—5.
*Number of petaloids.*—None.
*Shape of petals.*—Obovate, base acute or attenuate, upper end is rounded, margin is entire.
*Size of petals.*—Upper petals: 25–27 mm long, 22–24 mm wide; lower petals: 22–24 mm long, 21–22 mm wide.
*Color (general tonality from a distance of three meters)*.—Bluish-pink with white eyes.
*Color of upper petals.*—Main part near RHS 67 C, and almost white bases, RHS 69 D, covering about the lower third of the petals.
*Markings of upper petals.*—Two reddish-pink veins, RHS N66 B.
*Color of lower petals.*—RHS N74 B.
*Markings of lower petals.*—None.
*Color of lower surface of petals.*—Approximately RHS 71 D, with reddish veins, RHS N66 B.
*Color of sepals.*—Outer surface: mainly light green, RHS 144 A, near base RHS 179; inner surface: mainly light green, RHS 144 B, near base RHS 179 A.
*Number of sepals.*—5.
*Shape of sepals.*—Linear to lanceolate, acute tip, truncate base, surface with very weak pubescence, margin entire.
*Size of sepals.*—10–12 mm long, 4–5 mm wide for the largest upper sepal, 3 mm in width for the other sepals.

Bud: (just prior to petals unfolding)

*Shape.*—Elliptical to wide elliptical.
*Color of sepals.*—Light green, RHS 143 C.
*Color of petals.*—RHS 45 B.
*Length.*—15 mm.
*Width.*—10–11 mm.

REPRODUCTIVE ORGANS

*Androecium.*—3–5 fertile anthers, moderate pollen, yellow-orange, RHS 23 A, filaments white, RHS 155 D, to pink, RHS N 66 D.
*Gynoecium.*—One pistil, purple-pink style, RHS 61 C, 5–6-lobed stigma, purple, RHS 61 A.
*Fertility/seed set.*—Occasionally a few seeds are developed, mainly in late summer to fall.
*Fruit.*—Oblong, about 5–6 mm wide, rostrum (beak) 38–40 mm long.
*Seed.*—Oblong, 4–5 mm long, brown, RHS 177 B.

Spring flowering response period: In Hillscheid, Germany, in 2001, plants had on average 0.3 flowers opened 8 weeks after planting of rooted cuttings.

Outdoor flower production: Continuously and moderately rich flowering, the flower count in 2003 in Hillscheid, Germany, indicated about 1.8 inflorescences per plant in mid May Durability: Good stability of flower color, good rain resistance.

Lastingness of the individual flower: About 7–8 days at 18° C., about 15 days for the umbel.

Fragrance: None.

PLANT

Foliage:

*Shape.*—Kidney-shaped, with cordate base, with the gap between the lowest lobes open to almost closed, apex rounded with weak lobes.
*Margin.*—Bicrenate.
*Texture.*—Upper surface smooth, dull.
*Size of leaf.*—125 mm wide, 68 mm long.
*Color of upper surface.*—Medium green, approximately RHS 137 C.
*Color of zonation.*—Brown, about RHS 166 A, distinctness weak to medium.
*Color of lower surface.*—RHS 138 A.
*Petioles.*—Approximately 8–11 cm long, 3–3.5 mm diameter, light green in color, approximately RHS 143 B.

General appearance and form:

*Stem color.*—Light green, RHS 143 B.
*Internode length.*—20–40 mm.
*Branching pattern.*—5–6 branches.
*Size of plants.*—22.8 cm height, 35.3 wide (11-week-old plants, as described, measured from the top of the soil (base of the main stem) to the surface of the foliage canopy, without inflorescences.

I claim:

1. A new and distinct cultivar of *geranium* plant named 'Fip 469', as described and illustrated herein.

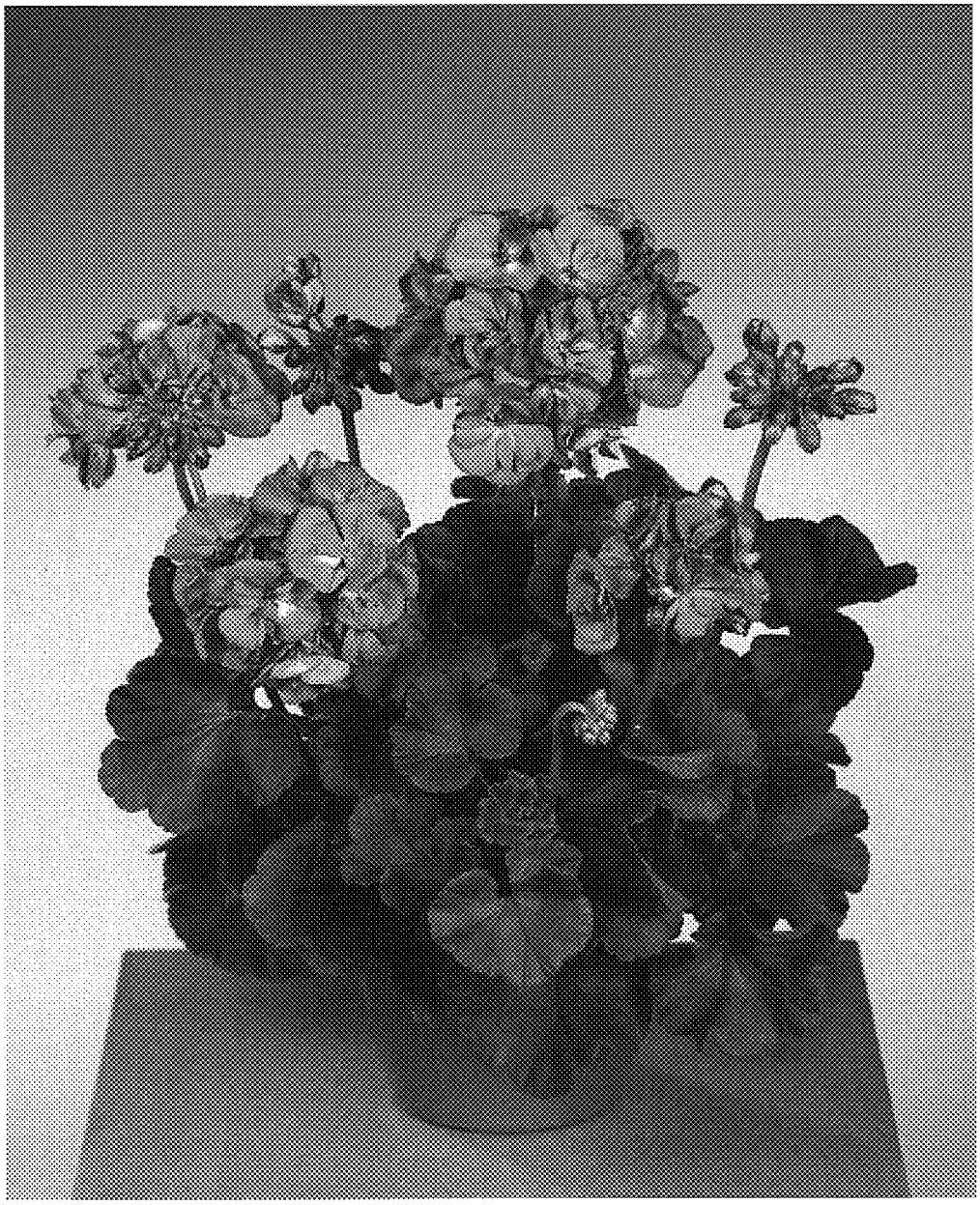

* * * * *